US007122174B2

(12) United States Patent
Nguyen et al.

(10) Patent No.: US 7,122,174 B2
(45) Date of Patent: Oct. 17, 2006

(54) COMPOSITIONS COMPRISING AT LEAST ONE SILICONE COMPOUND AND AT LEAST ONE AMINE COMPOUND, AND METHODS FOR USING THE SAME

(75) Inventors: Nghi Van Nguyen, Edison, NJ (US); Hitendra Mathur, Woodbridge, NJ (US); David W. Cannell, Plainfield, NJ (US)

(73) Assignee: L'Oreal S.A., Paris (FR)

( * ) Notice: Subject to any disclaimer, the term of this patent is extended or adjusted under 35 U.S.C. 154(b) by 461 days.

(21) Appl. No.: 10/259,742

(22) Filed: Sep. 30, 2002

(65) Prior Publication Data

US 2004/0062737 A1    Apr. 1, 2004

(51) Int. Cl.
*A61Q 5/12* (2006.01)
(52) U.S. Cl. .................. 424/70.12; 424/70.17
(58) Field of Classification Search ............. None
See application file for complete search history.

(56) References Cited

U.S. PATENT DOCUMENTS

| | | | |
|---|---|---|---|
| 4,423,032 A | 12/1983 | Abe et al. ............ 548/110 |
| 4,479,893 A | 10/1984 | Hirota et al. | |
| 4,704,272 A | 11/1987 | Oh et al. | |
| 5,070,171 A | 12/1991 | O'Lenick et al. | |
| 5,091,493 A | 2/1992 | O'Lenick, Jr. et al. | |
| 5,093,452 A | 3/1992 | O'Lenick, Jr. | |
| 5,100,956 A | 3/1992 | O'Lenick, Jr. | |
| 5,149,765 A | 9/1992 | O'Lenick, Jr. | |
| 5,237,035 A | 8/1993 | O'Lenick, Jr. et al. | |
| 5,248,783 A | 9/1993 | O'Lenick | |
| 5,260,055 A | 11/1993 | Imperante et al. ....... 424/71 |
| 5,275,755 A | 1/1994 | Sebag et al. | |
| 5,332,569 A | 7/1994 | Wood et al. | |
| 5,360,581 A * | 11/1994 | Rizvi et al. ............ 510/122 |
| 5,362,484 A | 11/1994 | Wood et al. | |
| 5,382,381 A | 1/1995 | Imperante et al. | |
| 5,587,155 A | 12/1996 | Ochiai et al. | |
| 5,739,371 A | 4/1998 | O'Lenick, Jr. | |
| 5,849,313 A | 12/1998 | Fost et al. | |
| 5,854,319 A | 12/1998 | O'Lenick, Jr. et al. | |
| 5,859,161 A | 1/1999 | Imperante et al. | |
| 5,976,519 A | 11/1999 | Nojiri et al. | |
| 5,997,853 A | 12/1999 | Bolich, Jr. et al. | |
| 6,175,028 B1 | 1/2001 | O'Lenick, Jr. | |
| 6,225,489 B1 | 5/2001 | Fost et al. | |
| 6,238,656 B1 | 5/2001 | Morita et al. | |
| 6,245,924 B1 | 6/2001 | Imperante | |
| 6,255,262 B1 | 7/2001 | Keenan et al. | |
| 6,358,501 B1 | 3/2002 | Dietz et al. | |
| 6,506,375 B1 * | 1/2003 | Barr ............... 424/74 |
| 2001/0037100 A1 | 11/2001 | Shanklin | |
| 2001/0053376 A1 | 12/2001 | Iwai et al. | |
| 2002/0002357 A1 | 1/2002 | Suzuki | |
| 2002/0022037 A1 | 2/2002 | Kurosawa et al. | |
| 2002/0058776 A1 | 5/2002 | Fost et al. | |
| 2002/0146381 A1 | 10/2002 | Aeby et al. | |

FOREIGN PATENT DOCUMENTS

| | | |
|---|---|---|
| DE | 195 36 420 A1 | 4/1996 |
| EP | 0 077 920 A2 | 4/1983 |
| EP | 0 186 507 A2 | 7/1986 |
| EP | 0 402 674 A2 | 12/1990 |
| EP | 0 470 613 A1 | 2/1992 |
| EP | 0 535 367 A2 | 4/1993 |
| EP | 0 615 741 A1 | 9/1994 |
| EP | 0 634 161 A1 | 1/1995 |
| EP | 0 654 259 A1 | 5/1995 |
| EP | 0 751 170 A2 | 6/1995 |
| EP | 0 758 547 A1 | 8/1995 |
| EP | 0 818 193 A2 | 7/1996 |
| EP | 0 882 673 A1 | 8/1997 |
| EP | 0 970 741 A1 | 1/1999 |
| EP | 1 013 705 A2 | 6/2000 |
| EP | 1 041 190 A2 | 10/2000 |
| EP | 1 068 859 A1 | 1/2001 |
| EP | 1 101 487 A1 | 5/2001 |
| EP | 1 142 551 A1 | 10/2001 |
| EP | 1 145 704 A1 | 10/2001 |
| EP | 1 155 667 A2 | 11/2001 |
| GB | 2 274 585 A | 8/1994 |
| GB | 2 291 804 A | 2/1996 |
| GB | 2 299 022 A | 9/1996 |
| GB | 2 299 023 A | 9/1996 |
| GB | 2 315 215 A | 1/1998 |
| GB | 2 320 432 A | 6/1998 |
| JP | 4117472 | 4/1992 |
| JP | 6345975 | 12/1994 |
| JP | 9048855 | 2/1997 |
| WO | WO 93/25179 | 12/1993 |
| WO | WO 94/02111 | 2/1994 |
| WO | WO 94/08555 | 4/1994 |
| WO | WO 95/04537 | 2/1995 |
| WO | WO 95/09598 | 4/1995 |
| WO | WO 95/18096 | 7/1995 |
| WO | WO 96/03962 | 2/1996 |
| WO | WO 96/03964 | 2/1996 |
| WO | WO 96/04884 | 2/1996 |
| WO | WO 96/04894 | 2/1996 |
| WO | WO 97/20540 | 6/1997 |
| WO | WO 97/44049 | 11/1997 |

(Continued)

OTHER PUBLICATIONS

Siltech Corp., "Silicone Carboxylates," available at http://www.siltechcorp.com/prod/SF.html, (2001), retrieved on Nov. 24, 2003.

(Continued)

*Primary Examiner*—Jyothsna Venkat
(74) *Attorney, Agent, or Firm*—Finnegan, Henderson, Farabow, Garrett & Dunner L.L.P.

(57) ABSTRACT

Compositions, methods, and kits for caring for, treating, conditioning or durable conditioning of at least one keratinous fiber comprising at least one silicone compound comprising at least one carboxylic acid group compound and at least one amine compound comprising at least two amino groups, wherein the amino groups are identical or different.

35 Claims, No Drawings

FOREIGN PATENT DOCUMENTS

| | | |
|---|---|---|
| WO | WO 97/49375 | 12/1997 |
| WO | WO 98/10741 | 3/1998 |
| WO | WO 98/24871 | 6/1998 |
| WO | WO 98/47470 | 10/1998 |
| WO | WO 98/56343 | 12/1998 |
| WO | WO 98/56344 | 12/1998 |
| WO | WO 98/56345 | 12/1998 |
| WO | WO 99/02124 | 1/1999 |
| WO | WO 99/04753 | 2/1999 |
| WO | WO 99/40407 | 8/1999 |
| WO | WO 00/10513 | 3/2000 |
| WO | WO 00/29521 | 5/2000 |
| WO | WO 00/63487 | 10/2000 |
| WO | WO 00/75164 | 12/2000 |
| WO | WO 01/78663 | 10/2001 |

OTHER PUBLICATIONS

European Search Report dated Nov. 24, 2003.
Patent Abstract, Japanese Publication No. 2001226689 A2, Application No. 2000033583, Publication Date: Aug. 21, 2001.
Patent Abstract, Japanese Publication No. 2000327786 A, Application No. 11143184, Publication Date: Nov. 28, 2000.
Patent Abstract, Japanese Publication No. 11061651 A, Application No. 09213038, Publication Date: Mar. 5, 1999.
DERWENT Abstract for DE 195 36 420 A1.
DERWENT Abstract for JP 4117472, Apr. 17, 1992.
DERWENT Abstract for JP 9048855, Publication Date: Feb. 18, 1997.
DERWENT Abstract for JP 6345975, Publication Date: Dec. 20, 1994.
Co-Pending U.S. Appl. No. 09/385,003, filed Aug. 27, 1999, Inventors: Jean-Michel Sturla et al., Title: Compositions Containing a Polycondensate Comprising at Least One Polyurethane and/or Polyurea Unit and a Silicone Comprising at Least One Carboxylic Function.
Co-Pending U.S. Appl. No. 10/259,741, filed Sep. 30, 2002, Inventors: Nghi Van Nguyen et al. Title: Compositions Comprising at Least One Silicone Phosphate Compound and at Least One Amine Compound, and Methods for Using the Same.

\* cited by examiner

COMPOSITIONS COMPRISING AT LEAST ONE SILICONE COMPOUND AND AT LEAST ONE AMINE COMPOUND, AND METHODS FOR USING THE SAME

The present invention relates to compositions, kits comprising these compositions, and methods for using these compositions for care, treatment, conditioning or durable conditioning of at least one keratinous fiber, including at least one human keratinous fiber, comprising at least one silicone compound comprising at least one carboxylic acid group and at least one amine compound comprising at least two amino groups, wherein the at least two amino groups are identical or different.

Shampoos generally comprise surfactants, such as anionic surfactants, to clean the hair. It is known that anionic surfactants not only remove the dirt and soil but also remove the naturally-present sebum from hair. Thus, shampoos may leave the hair dull and dry, that is, with what is known in the art as "creak." This generally makes the hair extremely difficult to comb either wet or dry, and once dry, the hair may not be amenable to styling, and may have undesirable electrostatic properties, causing the hair to "fly away." Due to the unsatisfactory condition of shampooed hair, many consumers use a conditioning composition to improve at least one of these undesirable characteristics.

Conditioning agents include cationic compounds such as cationic surfactants and cationic polymers which may render the hair more manageable, at least temporarily. For example, quaternized ammonium compounds may be used as hair conditioning agents. These compounds may be substantive to the hair due to the ionic interaction between their positive charge on the ammonium nitrogen atom and negative charges on the surface of the hair fibers. This ionic interaction, in effect, allows the conditioning agents to coat the hair shaft and thereby prevent tangling and matting of the individual hair fibers. Thus, the ability of these cationic compounds to adsorb to and/or react with the keratinous material of the hair makes them desirable compounds for conditioning the hair, such as for detangling wet hair and imparting manageability to dry hair.

However, the effect of these conditioning agents may not be long lasting. Normally, because of the weak ionic bond between the quaternized ammonium compounds and the hair fiber, the quaternized ammonium compounds are washed off the hair easily. This is especially true during shampooing, wherein anionic surfactants are present, generally in high concentrations. In such a case, the anionic surfactants in the shampoo and the cationic conditioning agents are known to form a complex which may be easily removed from the hair during the shampooing and/or which decreases the cleansing capabilities of the anionic surfactant and the conditioning capabilities of the conditioning agent.

Further, certain silicone compounds have been used as conditioning agents. However, these compounds lack durability on the hair shaft as these compounds are generally hydrophobic. Accordingly, silicone compounds may not be deposited on the hair, or are easily removed due to their weak hydrophobic interactions with the keratinous material of the hair.

Accordingly, in practice, most consumers prefer to apply an anionic surfactant-based shampoo to cleanse the hair, then rinse the hair, follow rinsing by application of a conditioner composition including a conditioning agent, such as, for example, a cationic compound, to condition the hair, and then rinse the hair again. As discussed above, this may only lead to temporary conditioning of the hair, as the next shampoo may remove the majority of the conditioning agents from the hair. Thus, there is a need for compositions and methods that condition hair, such as, for example, that impart a durable conditioning to the hair.

Compositions containing certain silicone compounds, certain amine compounds and certain silicone compounds comprising an amino group have previously been disclosed. For example, silicone emulsions containing amino acids are disclosed in U.S. Pat. No. 5,854,319, the disclosure of which is incorporated herein by reference. This emulsion contains (a) a silanol, (b) an alkoxy silicone crosslinking agent, (c) a water soluble amino compound, (d) an emulsifier, and (e) water. This patent also discloses a method for treating hair which comprises contacting the hair with an effective conditioning amount of the patented composition, allowing the contacted hair to dry and in a preferred embodiment, applying heat from a blow drier to accelerate crosslinking.

Further, for example, high foaming surfactants are disclosed in U.S. Pat. No. 5,248,783, the disclosure of which is incorporated herein by reference. The surfactants are silicone compounds containing carboxyl groups which are neutralized with organic amines. The organic amines may be chosen from alkyl tertiary amines, alkyl amido amines, alkyl N-bis-hydroxy amines, and imidazoline amines. However, these compounds may not impart durable conditioning to at least one keratinous fiber, and may not react to condition keratinous fibers in a synergistic manner.

Finally, U.S. Pat. No. 5,739,371, the disclosure of which is incorporated herein by reference, discloses carboxy silicone amphoteric surfactant complexes. These surfactants comprise a carboxy silicone wherein the carboxy group is neutralized with a tertiary amine having a specific formula. These salts may provide both detergency and conditioning to hair in a single application.

In essence, certain silicone compounds and certain amine compounds have been applied to hair for numerous reasons from conditioning to cleansing. Clearly, however, not all silicone compounds are the same, nor are all amine compounds the same, and thus not all combinations of silicone compounds and amine compounds impart the same properties when applied to a keratinous fiber.

The inventors have envisaged the application to at least one keratinous fiber at least one silicone compound comprising at least one carboxylic acid group and at least one amine compound comprising at least two amino groups, wherein the at least two amino groups are identical or different. In particular, the inventors have discovered that such compositions, and methods comprising applying these compositions to at least one keratinous fiber condition the at least one keratinous fiber. The compositions of the invention may also be used to care for, or treat, the at least one keratinous fiber. Further, in one embodiment, the inventive compositions impart a durable conditioning to the at least one keratinous fiber.

Thus, to achieve at least one of these and other advantages, the present invention, in one aspect, provides a composition for conditioning at least one keratinous fiber comprising at least one silicone compound comprising at least one carboxylic acid group and at least one amine compound comprising at least two amino groups, wherein the at least two amino groups may be identical or different, and further wherein the at least one silicone compound and the at least one amine compound are present in a combined amount effective to condition the at least one keratinous fiber, with the proviso that when the at least one silicone compound is chosen from silicone compounds of formula (V) and salts thereof as defined below, the at least one amine compound is not wheat protein or soy protein. In one embodiment, the at least one silicone compound and the at least one amine compound are present in a combined amount effective to durably condition the at least one keratinous fiber. In one embodiment, the at least one silicone compound and the at least one amine compound are present in the inventive composition in a synergistically effective amount to condition at least one keratinous fiber.

In another embodiment, the present invention provides a composition for durable conditioning of at least one keratinous fiber comprising at least one silicone compound comprising at least one carboxylic acid group and at least one amine compound comprising at least two amino groups, wherein the at least two amino groups may be identical or different, and further wherein the at least one silicone compound and the at least one amine compound are present in a combined amount effective to durably condition the at least one keratinous fiber, with the proviso that when the at least one silicone compound is chosen from silicone compounds of formula (V) and salts thereof as defined below, the at least one amine compound is not wheat protein or soy protein. In one embodiment, the at least one silicone compound and the at least one amine compound are present in the inventive composition in a synergistically effective amount to durably condition at least one keratinous fiber.

In another embodiment, the present invention is drawn to a method for conditioning at least one keratinous fiber comprising applying to the at least one keratinous fiber at least one silicone compound comprising at least one carboxylic acid group and at least one amine compound comprising at least two amino groups, wherein the at least two amino groups may be identical or different, and further wherein the at least one silicone compound and the at least one amine compound are present in a combined amount effective to condition the at least one keratinous fiber, with the proviso that when the at least one silicone compound is chosen from silicone compounds of formula (V) and salts thereof as defined below, the at least one amine compound is not wheat protein or soy protein. In one embodiment, the at least one silicone compound and the at least one amine compound are present in the inventive composition in a synergistically effective amount to condition at least one keratinous fiber. The at least one keratinous fiber may be rinsed after the application. The at least one keratinous fiber may be wet with water prior to application of the composition.

In another embodiment, the present invention is drawn to a method for durably conditioning for or treating at least one keratinous fiber comprising applying to the at least one keratinous fiber at least one silicone compound comprising at least one carboxylic acid group and at least one amine compound comprising at least two amino groups, wherein the at least two amino groups may be identical or different, and further wherein the at least one silicone compound and the at least one amine compound are present in a combined amount effective to durably condition the at least one keratinous fiber. In one embodiment, the at least one silicone compound and the at least one amine compound are present in the inventive composition in a synergistically effective amount to durably condition at least one keratinous fiber, with the proviso that when the at least one silicone compound is chosen from silicone compounds of formula (V) and salts thereof as defined below, the at least one amine compound is not wheat protein or soy protein. The at least one keratinous fiber may be rinsed after the application. The at least one keratinous fiber may be wet with water prior to application of the composition.

In another embodiment, the present invention is drawn to a method for caring for or treating at least one keratinous fiber comprising applying to the at least one keratinous fiber at least one silicone compound comprising at least one carboxylic acid group and at least one amine compound comprising at least two amino groups, wherein the at least two amino groups may be identical or different, and further wherein the at least one silicone compound and the at least one amine compound are present in a combined amount effective to condition the at least one keratinous fiber, with the proviso that when the at least one silicone compound is chosen from silicone compounds of formula (V) and salts thereof as defined below, the at least one amine compound is not wheat protein or soy protein. In one embodiment, the at least one silicone compound and the at least one amine compound are present in the inventive composition in a synergistically effective amount to condition at least one keratinous fiber. The at least one keratinous fiber may be rinsed after the application. The at least one keratinous fiber may be wet with water prior to application of the composition.

In yet another embodiment, the present invention provides a kit for caring for, treating, conditioning, or durably conditioning comprising at least two compartments, wherein a first compartment comprises a first composition comprising at least one silicone compound comprising at least one carboxylic acid group, and wherein a second compartment comprises a second composition comprising at least one amine compound comprising at least two amino groups, wherein the at least two amino groups are identical or different.

The present invention also provides compositions, kits comprising these compositions, and methods for using these compositions for care, treatment, conditioning or durable conditioning of at least one keratinous fiber, including at least one human keratinous fiber, comprising at least one silicone compound comprising at least one carboxylic acid group and at least one compound chosen from at least one amine compound comprising at least two amino groups as defined herein, silicone compounds comprising at least one amino group different from the at least one silicone compound comprising at least one carboxylic acid group, aminosilicone compounds comprising at least one amino group wherein the aminosilicone compounds are different from the at least one silicone compound comprising at least one carboxylic acid group, aminated polysaccharides comprising at least one amino group, hydrolysates of aminated polysaccharides comprising at least one amino group, and aminated monosaccharides comprising at least one amino group, wherein the at least one silicone compound and the at least one compound are present in a combined amount effective to condition the at least one keratinous fiber.

Certain terms used herein are defined below:

"Amino groups" as defined herein includes primary amino groups, secondary amino groups, and tertiary amino groups, and further includes amino groups which are terminal, pendant, and intercalated in a skeleton of the at least one amine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in). See Example 1.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Durable conditioning" as used herein, means that, following at least six shampoos after treatment, treated hair remains in a more conditioned state as compared to untreated hair.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain, wherein the at least one heteroatom is different from the at least two amino groups.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Keratinous fiber" as defined herein may be human keratinous fiber, and may be chosen from, for example, hair, eyelashes, and eyebrows.

"Ethylene oxide group" as defined herein refers to a group of formula —$CH_2CH_2$—O—.

"Propylene oxide group" as defined herein includes groups of formula —$CH_2CH_2CH_2$—O—, groups of formula ($CH_3$)$CHCH_2$—O—, and groups of formula —$CH_2(CH_3)CH$—O—.

"Polymers," as defined herein, include homopolymers and copolymers formed from at least two different types of monomers.

"Synergy," refers to the phenomenon in which the effect of at least two components (e.g., the at least one silicone compound comprising at least one carboxylic acid group and the at least one amine compound comprising at least two amino groups) is more than additive, i.e., the effect observed with the at least two components is greater than that observed for either component alone.

It is to be understood that both the foregoing general description and the following detailed description are exemplary and explanatory only and are not restrictive of the invention, as claimed. Reference will now be made in detail to exemplary embodiments of the present invention.

As described above, certain silicone compounds and certain amine compounds have been used in hair care compositions and other treatments for their detergency, surfactant and/or conditioning effect. However, it was unexpectedly discovered by the present inventors that a composition comprising at least one silicone compound chosen from a certain class of silicone compounds and at least one amine compound chosen from a certain class of amine compounds had at least one property that make it particularly desirable for use on keratinous fibers. For example, with respect to hair, compositions comprising at least one silicone compound comprising at least one carboxylic acid group and at least one amine compound comprising at least two amino groups (which amino groups may be identical or different) were found to condition the hair and also found to be useful in caring for and treating the hair. Further, these compositions may impart to the at least one keratinous fiber a durable conditioning even after shampooing the at least one keratinous fiber subsequent to treatment with such a composition.

Thus, in one embodiment, the present invention provides compositions for conditioning at least one keratinous fiber comprising at least one silicone compound comprising at least one carboxylic acid group and at least one amine compound comprising at least two amino groups, wherein the at least two amino groups may be identical or different, and further wherein the at least one silicone compound and the at least one amine compound are present in a combined amount effective to condition the at least one keratinous fiber, with the proviso that when the at least one silicone compound is chosen from silicone compounds of formula (V) and salts thereof as defined below, the at least one amine compound is not wheat protein or soy protein. In one embodiment, the at least one silicone compound and the at least one amine compound are present in the inventive composition in a synergistically effective amount to condition at least one keratinous fiber.

Silicone compounds of formula (V) have the following formula:

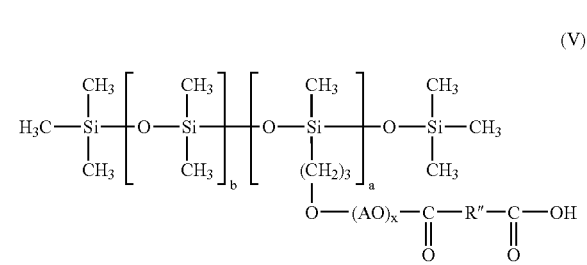

wherein:

a is an integer ranging from 1 to 100;

b is an integer ranging from 0 to 500;

AO is chosen from groups of formula (VI):

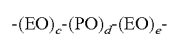

wherein:
c, d, and e, which may be identical or different, are each integers ranging from 0 to 20;
EO is an ethylene oxide group; and
PO is a propylene oxide group;
x is an integer ranging from 0 to 60;
R" is chosen from optionally substituted divalent hydrocarbons, such as alkylene groups and alkenylene groups comprising from 2 to 22 carbon atoms, and optionally substituted divalent aromatic groups, such as groups of formula (III):

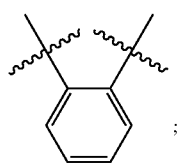

(III)

and
groups of formula (IV):

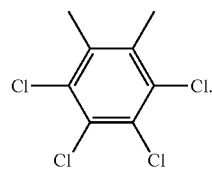

(IV)

According to the present invention, in some cases, the ratio of amino groups in the at least one amine compound to carboxylic acid groups in the at least one silicone compound may not be determinative of the effectiveness of the inventive compositions in conditioning at least one keratinous fiber as long as the at least one amine compound comprises at least two amino groups. For example, the examples below show that the molecular weight, the amine value, and/or the nature of the amino groups of the at least one amine compound may affect the effectiveness of the composition comprising at least one silicone compound and the at least one amine compound in conditioning at least one keratinous fiber.

According to the present invention, the at least one silicone compound comprising at least one carboxylic acid group may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

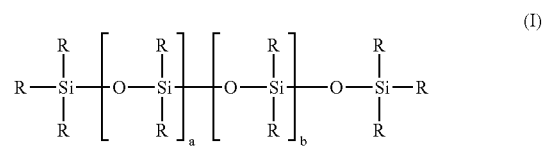

(I)

wherein:
a is an integer ranging from 1 to 100;
b is an integer ranging from 0 to 500;
R, which may be identical or different, are each chosen from optionally substituted hydrocarbon groups comprising from 1 to 9 carbon atoms, optionally substituted phenyl groups, and groups of formula (II):

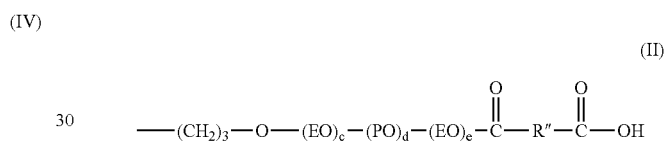

(II)

wherein:
c, d, and e, which may be identical or different, are each integers ranging from 0 to 20;
EO is an ethylene oxide group;
PO is a propylene oxide group; and
R" is chosen from optionally substituted divalent hydrocarbons, such as alkylene groups and alkenylene groups comprising from 2 to 22 carbon atoms, and optionally substituted divalent aromatic groups, such as groups of formula (III):

(III)

and
groups of formula (IV):

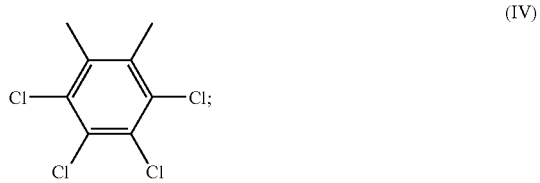

(IV)

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from BF Goodrich under the name Lubricant CPI and those commercially available from Siltech Corp. under the name Silube CP-I, both of which have the formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

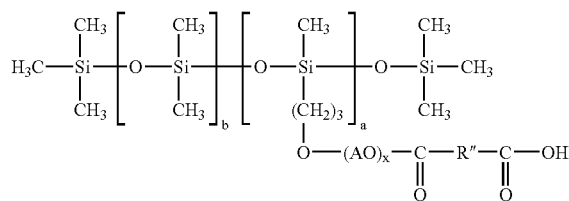
(V)

wherein:
a is an integer ranging from 1 to 100;
b is an integer ranging from 0 to 500;
AO is chosen from groups of formula (VI):

(VI)

wherein:
c, d, and e, which may be identical or different, are each integers ranging from 0 to 20;
EO is an ethylene oxide group; and
PO is a propylene oxide group;
x is an integer ranging from 0 to 60;
R'' is chosen from optionally substituted divalent hydrocarbons, such as alkylene groups and alkenylene groups comprising from 2 to 22 carbon atoms, and optionally substituted divalent aromatic groups, such as groups of formula (III):

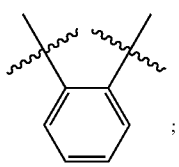
(III)

and
groups of formula (IV):

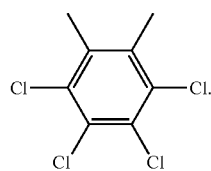
(IV)

Non-limiting examples of the at least one silicone compound include those described in U.S. Pat. Nos. 5,248,783 and 5,739,371, the disclosures of which are incorporated herein by reference, and which are silicone compounds of formula (I).

In one embodiment, the at least one silicone compound is present in the inventive composition in an amount ranging from 0.01% to 30% by weight relative to the total weight of the composition. In another embodiment, the at least one silicone compound is present in an amount ranging from 0.1% to 15% by weight relative to the total weight of the composition. One of ordinary skill in the art will recognize that the at least one silicone compound according to the present invention may be commercially available, and may come from suppliers in the form of a dilute solution. The amounts of the at least one silicone compound disclosed herein therefore reflect the weight percent of active material.

As previously defined, the at least two amino groups of the at least one amine compound are chosen from primary amino groups, secondary amino groups and tertiary amino groups. In one embodiment, the at least two amino groups are identical. In another embodiment, the at least two amino groups are different.

The at least one amine compound of the present invention comprises at least two amino groups. In one embodiment, the at least one amine compound comprises at least three amino groups, such as greater than three amino groups. In another embodiment, the at least one amine compound comprises at least four amino groups, such as greater than four amino groups. In another embodiment, the at least one amine compound comprises at least five amino groups, such as greater than five amino groups. In another embodiment, the at least one amine compound comprises at least ten amino groups, such as greater than ten amino groups.

The at least one amine compound of the present invention may, for example, be chosen from hydrocarbons comprising at least two amino groups, and silicone compounds comprising at least two amino groups different from the at least one silicone compound comprising at least one carboxylic acid group. In one embodiment of the present invention, the at least one amine compound may, for example, be chosen from aminosilicone compounds comprising at least two amino groups wherein the aminosilicone compounds are different from the at least one silicone compound comprising at least one carboxylic acid group. Non-limiting examples of suitable aminosilicone compounds comprising at least two amino groups are DC 2-8566 and DC 2-8902, both of which are commercially available from Dow Corning. In one embodiment of the present invention, the at least one amine compound may, for example, be chosen from aminated polysaccharides comprising at least two amino groups, such as, for example, chitosan, and hydrolysates of aminated polysaccharides comprising at least two amino groups. In one embodiment, the at least one amine compound may, for example, be chosen from polymers. Suitable polymers for use as the at least one amine compound are polymers comprising at least two amino groups as defined herein. Non-limiting examples of suitable polymers include homopolymers comprising at least two amino groups and copolymers comprising at least two amino groups. Thus, the at least one amine compound comprising at least two amino groups may be chosen from, for example, polymers comprising at least two amino groups formed from (i) at least one monomer unit comprising at least two amino groups as defined herein, and, optionally, (ii) at least one additional monomer unit different from the at least one monomer (i); and polymers comprising at least two amino groups formed from (i) at least one monomer comprising at least one amino group as defined herein, and, optionally, (ii) at least one additional monomer unit different from the at least one monomer (i). According to the present invention, the at least one additional monomer different from the at least one monomer (i) may or may not comprise at least one amino group as defined herein.

In one embodiment of the present invention, the at least one amine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35, as well as Lupasol™ SC® Polyethyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

In another embodiment, the at least one amine compound comprising at least two amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000). In one embodiment, the at least one amine compound comprising at least two amino groups is chosen from wheat protein, soy protein, oat protein, collagen, and keratin protein. In one embodiment, the inventive composition comprises (a) at least one silicone compound chosen from silicone compounds of formula (V) and salts thereof, and (b) at least one amine compound comprising at least two amino groups, with the proviso that the at least one amine compound is not chosen from wheat protein and soy protein.

In one embodiment, the at least one amine compound comprising at least two amino groups is not chosen from proteins and protein derivatives. In one embodiment, the at least one amine compound comprising at least two amino groups is not chosen from compounds comprising lysine, compounds comprising arginine, and compounds comprising histidine. In one embodiment, the at least one amine compound comprising at least two amino groups is chosen from amino acid compounds and derivatives of amino acid compounds, such as, for example, lysine, arginine, histidine, and hydroxylysine.

In one embodiment, the at least one amine compound is present in the inventive composition in an amount ranging from 0.01% to 30% by weight relative to the total weight of the composition. In another embodiment, the at least one amine compound is present in an amount ranging from 0.1% to 15% by weight relative to the total weight of the composition. One of ordinary skill in the art will recognize that the at least one amine compound according to the present invention may be commercially available, and may come from suppliers in the form of a dilute solution. The amounts of the at least one amine compound disclosed herein therefore reflect the weight percent of active material.

In one embodiment of the present invention, the at least one silicone compound and the at least one amine compound are present in the inventive composition in a synergistically effective amount to condition at least one keratinous fiber. Example 1 provides for a simple screening test, the combability test (See Garcia, M. L., and Diaz, J., J. Soc. Cosmet. Chem. 27, 370–398 (1976)), to determine the presence of synergy and what constitutes a synergistically effective amount of the at least one silicone compound and the at least one amine compound in such mixtures. The combability test is known in the art to correlate well to the amount of conditioning that is afforded hair by a composition. Wet combing work of normal hair is determined prior to treatment. The hair is then divided into three groups and treated, one group with a composition comprising at least one silicone compound and the at least one amine compound, a second group with a control solution containing the at least one silicone compound alone, and a third group with a control solution containing the at least one amine compound alone. The increase in work or force required to comb wet hair is compared for hair treated with the inventive composition versus the hair treated with the controls to determine if a synergistic effect is observed.

The compositions of the present invention as well as those used in the methods of the present invention may, for example, be in the form of a shampoo, a conditioner, a hair dye, a hair bleach, a permanent waving product, a relaxing product, a styling product, or a hair care product, such as a hair treatment. The inventive compositions may further comprise at least one solvent. Non-limiting examples of the at least one solvent include water and organic solvents. Non-limiting examples of organic solvents include $C_1$–$C_4$ alkanols, such as ethanol and isopropanol; glycerol; glycols and glycol ethers, such as 2-butoxyethanol, propylene glycol, propylene glycol monomethyl ether, diethylene glycol monoethyl and monomethyl ether, and aromatic alcohols, such as benzyl alcohol and phenoxyethanol, and mixtures thereof. Further, the inventive compositions may be acidic or basic.

In one embodiment, these compositions may further comprise at least one suitable additive chosen from additives commonly used in compositions for keratinous fibers. Non-limiting examples of the at least one suitable additive include anionic surfactants different from the at least one silicone compound and from the at least one amine compound, cationic surfactants different from the at least one silicone compound and from the at least one amine compound, nonionic surfactants different from the at least one silicone compound and from the at least one amine compound, amphoteric surfactants different from the at least one silicone compound and from the at least one amine compound, zwitterionic surfactants different from the at least one silicone compound and from the at least one amine compound, thiol compounds, fragrances, penetrating agents, antioxidants, sequestering agents, opacifying agents, solubilizing agents, emollients, colorants, screening agents (such as sunscreens and UV filters), preserving agents, vitamins, silicones, polymers such as thickening polymers different from the at least one silicone compound and from the at least one amine compound, plant oils, mineral oils, synthetic oils and any other additive conventionally used in compositions for the conditioning, care and/or treatment of at least one keratinous fiber.

Needless to say, a person skilled in the art will take care to select the at least one suitable additive such that the advantageous properties of the composition in accordance with the invention are not, or are not substantially, adversely affected by the addition(s) envisaged.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contains certain errors necessarily resulting from the standard deviation found in their respective testing measurements. The following example is intended to illustrate the invention without limiting the scope as a result.

EXAMPLES

Example 1

Synergistic Effects of the Silicone Compound and the Amine Compound

A clear solution containing at least one silicone compound comprising at least one carboxylic acid group and at least one amine compound comprising at least two amino groups in a combined amount of 7% by weight relative to the total weight of the composition formed from Lubricant CPI (3.8% by weight relative to the total weight of the composition) and Lupasol PR8515 (3.2% by weight relative to the total weight of the composition) was used to treat bleached hair swatches (0.5 g of solution/g hair). The treatment consisted of applying the clear solution to the bleached hair swatches and leaving the solution on the hair for 2 minutes. After 2 minutes, the hair swatches were rinsed with warm water for 1 minute. Before and after treatment, the force needed to comb through the wet hair swatches was determined using an Instron Tensile Tester. The percent improvement (% improvement) is defined as:

% Improvement = $(W_b - W_a)/W_b \times 100\%$ where $W_b$ = Combing Work before treatment $W_a$ = Combing Work after treatment The same procedure was repeated with hair swatches that were treated with a solution containing Lubricant CPI sodium salt (7.6% by weight relative to the total weight of the composition) and hair swatches that were treated with a solution containing Lupasol PR8515 (6.4% by weight relative to the total weight of the composition). All results are the average of duplicate experiments. Table 1 shows the % improvement of the combability of hair swatches after the treatment.

TABLE 1

Synergy of at least one Silicone Compound and at least one Amine Compound

| Rinse-off Treatment | % Improvement |
| --- | --- |
| Polyethyleneimine Solution (6.4%) | 13.8 |
| Silicone Compound Solution (7.6%) | 8.4 |
| Silicone Compound and Polyethyleneimine Solution (7%: 3.8% CPI; 3.2% PEI) | 68.4 |

The data show that the % Improvement in wet combability of hair treated with the solution containing both the silicone compound and the amine compound is much greater than the % Improvement in wet combability of hair treated with either a polyethyleneimine solution or a silicone compound solution, despite the higher concentration of CPI and PEI in the latter. Thus, the inventive composition exhibits a synergistic effect compared to solutions comprising only one of the individual components.

Example 2

Durable Conditioning Effects of the Silicone Compound/Amine Compound Composition Following the procedure of Example 1, bleached hair swatches were treated with a solution containing a silicone compound/amine compound composition in a combined amount of 7% by weight relative to the total weight of the composition formed from Lubricant CPI and Lupasol PR8515. After the initial treatment and combing test, the wet combability test was also performed after the hair swatches were shampooed 3 times and 6 times with 10% SLES. For comparison, a similar experiment was performed using a solution containing 7% LEXQUAT® AMG-BEO. LEXQUAT® AMG-BEO (INCI: behenamidopropyl PG dimonium chloride), a common conditioning agent, is a cationic surfactant comprising at least one quaternary amino group and is commercially available, for example, from Inolex Chemical Company. The results are shown in Table 2.

TABLE 2

Durable Conditioning Effects of the Silicone Compound/Amine Compound Composition

| Rinse-off Treatment | % Improvement After Treatment | % Improvement After 3 Shampoos | % Improvement After 6 Shampoos |
| --- | --- | --- | --- |
| Silicone/Amine Composition | 68.4 | 63.3 | 47.9 |
| LEXQUAT ® AMG-BEO | 57.9 | 28.0 | −31.8 |

The results indicate that even after multiple shampoos the hair treated with the silicone/amine composition was still conditioned whereas hair treated with LEXQUAT lost all conditioning after 6 shampoos.

Example 3

Effects of the Molecular Weight of the Amine Compound on the Durability of the Conditioning by the Composition Following the procedure in Example 1, bleached hair swatches were treated with a series of solutions containing a silicone compound/amine compound composition in a combined amount of 7% by weight relative to the total weight of the composition. The amine compounds in the silicone compound/amine compound composition had similar amine values but increasing molecular weights. The results from the wet combability tests are shown in Table 3.

TABLE 3

Effects of the Molecular Weight of the Amine Compound

| Amine Compound | Average Number Molecular Weight of Amine Compound | Amine Value (meq/g) | % Improvement After Treatment | % Improvement After 3 Shampoos | % Improvement After 6 Shampoos |
|---|---|---|---|---|---|
| Epomin ™ SP-006 | 600 | 17.8 | 7.9 | −0.49 | −47.9 |
| Epomin ™ SP-012 | 1,200 | 16.4 | 32.4 | 23.2 | 18.5 |
| Epomin ™ SP-018 | 1,800 | 17.5 | 40.1 | 32.7 | 29.1 |
| Epomin ™ P-1000 | 70,000 | 18 | 69.5 | 57.0 | 42.6 |

The results indicate that the durable conditioning effects of the silicone compound/amine compound composition increased as did the molecular weight of the amine compound in the silicone compound/amine compound composition.

Example 4

Effects of the Amine Value of the Amine Compound on Durable Conditioning

Following the procedure in Example 1, bleached hair swatches were treated with a series of solutions containing a silicone compound/amine compound composition in a combined amount of 7% by weight relative to the total weight of the composition. The amine compounds in the silicone compound/amine compound composition had similar molecular weights but increasing amine values. The results from the wet combability tests are shown in Table 4.

TABLE 4

Effects of the Amine Value of the Amine Compound

| Amine Compound | Average Number Molecular Weight of Amine Compound | Amine Value (meq/g) | % Improvement After Treatment | % Improvement After 3 Shampoos | % Improvement After 6 Shampoos |
|---|---|---|---|---|---|
| Lupasol ™ PS | 60,000 | 18.2 | 44.5 | 41.6 | 39.1 |
| Lupasol ™ PL | 60,000 | 7.2 | 43.9 | 39.2 | 36.6 |

The trend shown in these results appears to indicate that the durable conditioning effects of the silicone compound/amine compound composition increased as did the amine value of the amine compound in the silicone compound/amine compound composition.

Example 5

Effects of the pH of the Silicone Compound/Amine Compound Composition on the Durable Conditioning Following the procedure in Example 1, bleached hair swatches were treated with one of two solutions containing a silicone compound/amine compound composition in a combined amount of 7% by weight relative to the total weight of the composition formed from Lubricant CPI and Lupasol PR8515 having an adjusted pH of 6.5 or 10.0. The results from the wet combability tests are shown in Table 5.

TABLE 5

Effects of the pH of the Silicone Compound/Amine Compound Composition

| pH of Solution | % Improvement After Treatment | % Improvement After 3 Shampoos | % Improvement After 6 Shampoos |
|---|---|---|---|
| 10.0 | 68.4 | 63.3 | 47.9 |
| 6.5 | 87.1 | 69.2 | 43.8 |

The results indicate that durable conditioning of hair is possible with either acidic or basic solutions comprising the silicone compound/amine compound composition.

Example 6

Effects of the Concentration of the Silicone Compound/Amine Compound Composition on the Durable Conditioning Following the procedure in Example 1, bleached hair swatches were treated with solutions containing a silicone compound/amine compound composition in a combined amount of 7% by weight, 5% by weight, or 3% by weight relative to the total weight of the composition formed from Lubricant CPI and Lupasol PR8515 having an adjusted pH of 6.5. The results from the wet combability tests are shown in Table 6.

TABLE 6

Effects of the Concentration of the Silicone Compound/Amine Compound Composition

| Concentration of Solution (%) | % Improvement After Treatment | % Improvement After 6 Shampoos |
|---|---|---|
| 7 | 87.1 | 43.8 |
| 5 | 82.1 | 34.2 |
| 3 | 80.0 | 43.1 |

The results indicate that durable conditioning of hair is possible with a solution comprising 3% of the silicone compound/amine compound.

What is claimed is:

1. A composition for conditioning at least one keratinous fiber comprising
   (a) at least one silicone compound comprising at least one carboxylic acid group chosen from:

(i) silicone compounds of formula (I) and salts thereof:

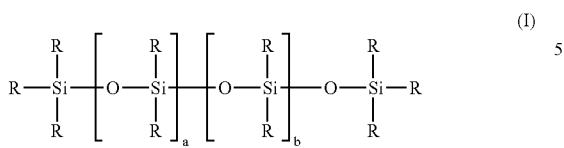

wherein:
  a is an integer ranging from 1 to 100;
  b is an integer ranging from 0 to 500;
  R, which may be identical or different, are each chosen from optionally substituted hydrocarbon groups comprising from 1 to 9 carbon atoms, optionally substituted phenyl groups, and groups of formula (II):

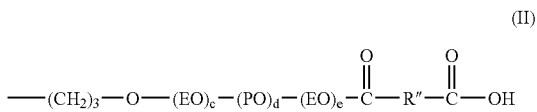

c, d, and e, which may be identical or different, are each integers ranging from 0 to 20;
  EO is an ethylene oxide group;
  PO is a propylene oxide group; and
  R" is chosen from optionally substituted divalent hydrocarbons and optionally substituted divalent aromatic groups;
with the proviso that at least one of the R groups is chosen from groups of formula (II) and
with the proviso that when only one of the R groups is chosen from groups of formula (II), the other R groups are not all methyl groups; and
(ii) silicone compounds of formula (V) and salts thereof:

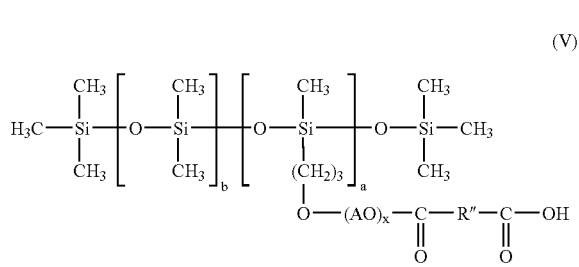

wherein:
  a is an integer ranging from 1 to 100;
  b is an integer ranging from 0 to 500;
  AO is chosen from groups of formula (VI):

c, d, and e, which may be identical or different, are each integers ranging from 0 to 20;
  EO is an ethylene oxide group;
  PO is a propylene oxide group; and
  R" is chosen from optionally substituted divalent hydrocarbons and optionally substituted divalent aromatic groups; and
(b) at least one amine compound comprising at least two amino groups, wherein said at least two amino groups are identical or different; and
wherein said at least one silicone compound and said at least one amine compound are present in a combined amount effective to condition the at least one keratinous fiber,
with the proviso that when said at least one silicone compound is chosen from silicone compounds of formula (V) and salts thereof then said at least one amine compound is not wheat protein or soy protein.

2. A composition according to claim 1, wherein said at least one silicone compound and said at least one amino compound are present in said composition in a synergistically effective amount to condition the at least one keratinous fiber.

3. A composition according to claim 1, wherein said at least one silicone compound and said at least one amine compound are present in a combined amount effective to dumbly condition said at least one keratinous fiber.

4. A composition according to claim 1, wherein said divalent hydrocarbons are chosen from alkylene groups comprising from 2 to 22 carbon atoms and alkenylene groups comprising from 2 to 22 carbon atoms.

5. A composition according to claim 1, wherein said divalent aromatic groups are chosen from groups of formula (III):

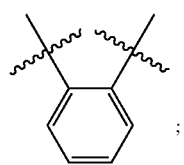

groups of formula (IV):

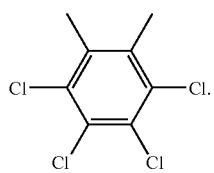

6. A composition according to claim 1, wherein said at least one silicone compound is present in an amount ranging from 0.01% to 30% by weight relative to the total weight of the composition.

7. A composition according to claim 6, wherein said at least one silicone compound is present in an amount ranging from 0.1% to 15% by weight relative to the total weight of the composition.

8. A composition according to claim 1, wherein said at least two amino groups are identical.

9. A composition according to claim 1, wherein said at least two amino groups are different.

10. A composition according to claim 1, wherein said at least two amino groups are chosen from primary amino groups, secondary amino groups and tertiary amino groups.

11. A composition according to claim 1, wherein said at least one amine compound comprising at least two amino groups is chosen from hydrocarbons comprising at least two amino groups, silicone compounds comprising at least two amino groups different from the at least one silicone compound comprising at least one carboxylic acid group, polysaccharides comprising at least two amino groups, and hydrolysates of polysaccharides comprising at least two amino groups.

12. A composition according to claim 1, wherein said at least one amine compound comprising at least two amino groups is chosen from polymers comprising at least two amino groups.

13. A composition according to claim 12, wherein said polymers comprising at least two amino groups are chosen from polyamines.

14. A composition according to claim 12, wherein said polyamines are chosen from homopolymers comprising at least two amino groups, copolymers comprising at least two amino groups, and terpolymers comprising at least two amino groups.

15. A composition according to claim 13, wherein said polyamines are chosen from polyethyleneimines.

16. A composition according to claim 1, wherein said at least one amine compound is chosen from proteins.

17. A composition according to claim 16, wherein said proteins are chosen from wheat protein, soy protein, oat protein, collagen and keratin protein.

18. A composition according to claim 1, wherein said at least one amine compound is present in an amount ranging from 0.01% to 30% by weight relative to the total weight of the composition.

19. A composition according to claim 18, wherein said at least one amine compound is present in an amount ranging from 0.1% to 15% by weight relative to the total weight of the composition.

20. A composition according to claim 1, wherein said composition is in the form of a shampoo, a conditioner, a hair dye, a permanent waving product, a relaxing product, or a styling product.

21. A composition according to claim 1, further comprising at least one solvent.

22. A composition according to claim 21, wherein said at least one solvent is chosen from water and organic solvents.

23. A composition according to claim 22, wherein said organic solvents are chosen from $C_1$–$C_4$ alkanols, glycerol, glycols, glycol ethers, aromatic alcohols, and mixtures thereof.

24. A composition according to claim 1, further comprising at least one additive chosen from anionic surfactants different from said at least one silicone compound and from said at least one amine compound, cationic surfactants different from said at least one silicone compound and from said at least one amine compound, nonionic surfactants different from said at least one silicone compound and from said at least one amine compound, amphoteric surfactants different from said at least one silicone compound and from said at least one amine compound, zwitterionic surfactants different from said at least one silicone compound and from said at least one amine compound, thiol compounds, fragrances, penetrating agents, antioxidants, sequestering agents, opacifying agents, solubilizing agents, emollients, colorants, screening agents, preserving agents, vitamins, silicones, polymers different from said at least one silicone compound and from said at least one amine compound, plant oils, mineral oils, and synthetic oils.

25. A composition for durable conditioning of at least one keratinous fiber comprising:
(a) at least one silicone compound comprising at least one carboxylic acid group chosen from:

(i) silicone compounds of formula (I) and salts thereof:

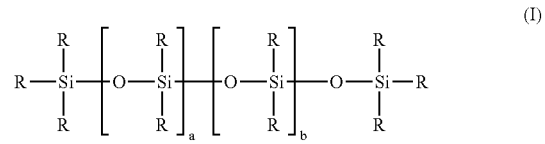

wherein:
a is an integer ranging from 1 to 100;
b is an integer ranging from 0 to 500;
R, which may be identical or different, are each chosen from optionally substituted hydrocarbon groups comprising from 1 to 9 carbon atoms, optionally substituted phenyl groups, and groups of formula (II):

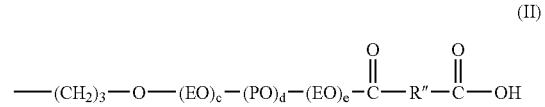

c, d, and e, which may be identical or different, are each integers ranging from 0 to 20;
EO is an ethylene oxide group;
PO is a propylene oxide group; and
R" is chosen from optionally substituted divalent hydrocarbons and optionally substituted divalent aromatic groups;
with the proviso that at least one of the R groups is chosen from groups of formula (II) and
with the proviso that when only one of the R groups is chosen from groups of formula (II), the other R groups are not all methyl groups; and (ii) silicone compounds of formula (V) and salts thereof:

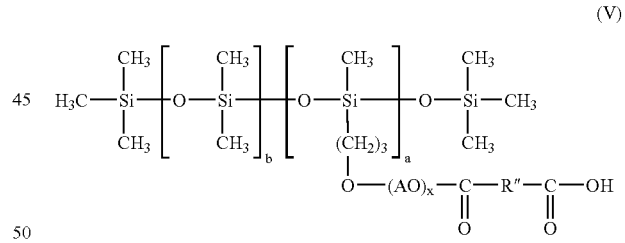

wherein:
a is an integer ranging from 1 to 100;
b is an integer ranging from 0 to 500;
AO is chosen from groups of formula (VI):

c, d, and e, which may be identical or different, are each integers ranging from 0 to 20;
EO is an ethylene oxide group;
PO is a propylene oxide group; and
R" is chosen from optionally substituted divalent hydrocarbons and optionally substituted divalent aromatic groups; and
(b) at least one amine compound comprising at least two amino groups, wherein said at least two amino groups are identical or different; and wherein said at least one silicone compound and said at least one amine compound are present in a combined amount effective to condition the at least one keratinous fiber, with the proviso that when said at least one silicone compound is chosen from silicone compounds of formula (V) and salts thereof then said at least one amine compound is not wheat protein or soy protein.

26. A method for conditioning at least one keratinous fiber comprising:

applying to said at least one keratinous fiber at least one composition comprising:

(a) at least one silicone compound comprising at least one carboxylic acid group chosen from:

(i) silicone compounds of formula (I) and salts thereof:

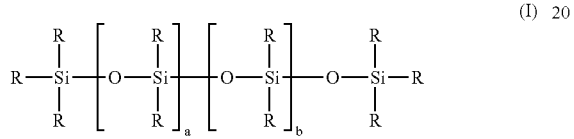

wherein:
a is an integer ranging from 1 to 100;
b is an integer ranging from 0 to 500;
R, which may be identical or different, are each chosen from optionally substituted hydrocarbon groups comprising from 1 to 9 carbon atoms, optionally substituted phenyl groups, and groups of formula (II):

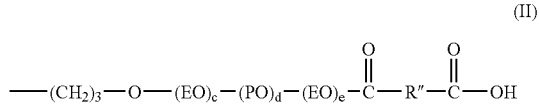

c, d, and e, which may be identical or different, are each integers ranging from 0 to 20;
EO is an ethylene oxide group;
PO is a propylene oxide group; and
R″ is chosen from optionally substituted divalent hydrocarbons and optionally substituted divalent aromatic groups;
with the proviso that at least one of the R groups is chosen from groups of formula (II) and
with the proviso that when only one of the R groups is chosen from groups of formula (II), the other R groups are not all methyl groups; and (ii) silicone compounds of formula (V) and salts thereof:

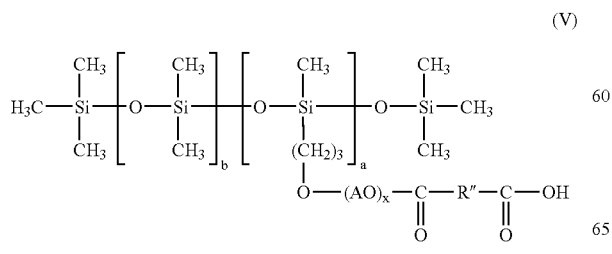

wherein:
a is an integer ranging from 1 to 100;
b is an integer ranging from 0 to 500;
AO is chosen from groups of formula (VI):

c, d, and e, which may be identical or different, are each integers ranging from 0 to 20;
EO is an ethylene oxide group;
PO is a propylene oxide group; and
R″ is chosen from optionally substituted divalent hydrocarbons and optionally substituted divalent aromatic groups; and (b) at least one amine compound comprising at least two amino groups, wherein said at least two amino groups are identical or different; and wherein said at least one silicone compound and said at least one amine compound are present in a combined amount effective to condition the at least one keratinous fiber, with the proviso that when said at least one silicone compound is chosen from silicone compounds of formula (V) and salts thereof then said at least one amine compound is not wheat protein or soy protein.

27. A method according to claim 26, further comprising wetting said at least one keratinous fiber with water prior to said application.

28. A method according to claim 26, further comprising rinsing said at least one keratinous fiber subsequent to said application.

29. A method for durably conditioning at least one keratinous fiber comprising;

applying to said at least one keratinous fiber at least one composition comprising:

(a) at least one silicone compound comprising at least one carboxylic acid group chosen from:

(i) silicone compounds of formula (I) and salts thereof:

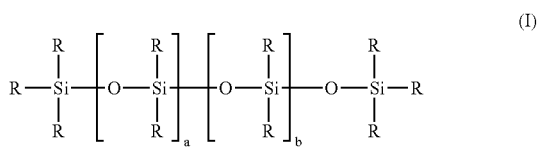

wherein:
a is an integer ranging from 1 to 100;
b is an integer ranging from 0 to 500;
R, which may be identical or different, are each chosen from optionally substituted hydrocarbon groups comprising from 1 to 9 carbon atoms, optionally substituted phenyl groups, and groups of formula (II):

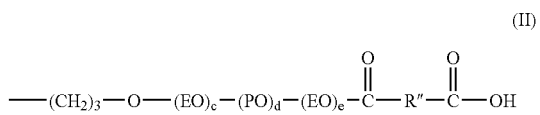

c, d, and e, which may be identical or different, are each integers ranging from 0 to 20;
EO is an ethylene oxide group;
PO is a propylene oxide group; and R" is chosen from optionally substituted divalent hydrocarbons and optionally substituted divalent aromatic groups;

with the proviso that at least one of the R groups is chosen from groups of formula (II) and with the proviso that when only one of the R groups is chosen from groups of formula (II), the other R groups are not all methyl groups; and (ii) silicone compounds of formula (V) and salts thereof:

$$H_3C-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_b-\left[O-\underset{\underset{\underset{\underset{O-(AO)_x-\overset{\overset{O}{\|}}{C}-R''-\overset{\overset{O}{\|}}{C}-OH}{|}}{(CH_2)_3}}{|}}{\overset{\overset{CH_3}{|}}{Si}}\right]_a-O-\underset{\underset{CH_3}{|}}{\overset{\overset{CH_3}{|}}{Si}}-CH_3 \qquad (V)$$

wherein:
a is an integer ranging from 1 to 100;
b is an integer ranging from 0 to 500;
AO is chosen from groups of formula (VI):

$$-(EO)_c-(PO)_d-(EO)_e- \qquad (VI)$$

c, d, and e, which may be identical or different, are each integers ranging from 0 to 20;
EO is an ethylene oxide group;
PO is a propylene oxide group; and
R" is chosen from optionally substituted divalent hydrocarbons and optionally substituted divalent aromatic groups; and (b) at least one amine compound comprising at least two amino groups, wherein said at least two amino groups are identical or different; and wherein said at least one silicone compound and said at least one amine compound are present in a combined amount effective to condition the at least one keratinous fiber, with the proviso that when said at least one silicone compound is chosen from silicone compounds of formula (V) and salts thereof then said at least one amine compound is not wheat protein or soy protein.

30. A method according to claim 29, further comprising wetting said at least one keratinous fiber with water prior to said application.

31. A method according to claim 29, further comprising rinsing said at least one keratinous fiber subsequent to said application.

32. A method for caring for or treating at least one keratinous fiber comprising:

applying to said at least one keratinous fiber at least one composition comprising:

(a) at least one silicone compound comprising at least one carboxylic acid group chosen from:

(i) silicone compounds of formula (I) and salts thereof:

$$R-\underset{\underset{R}{|}}{\overset{\overset{R}{|}}{Si}}-\left[O-\underset{\underset{R}{|}}{\overset{\overset{R}{|}}{Si}}\right]_a-\left[O-\underset{\underset{R}{|}}{\overset{\overset{R}{|}}{Si}}\right]_b-O-\underset{\underset{R}{|}}{\overset{\overset{R}{|}}{Si}}-R \qquad (I)$$

wherein:
a is an integer ranging from 1 to 100;
b is an integer ranging from 0 to 500;
R, which may be identical or different, are each chosen from optionally substituted hydrocarbon groups comprising from 1 to 9 carbon atoms, optionally substituted phenyl groups, and groups of formula (II):

$$-(CH_2)_3-O-(EO)_c-(PO)_d-(EO)_e-\overset{\overset{O}{\|}}{C}-R''-\overset{\overset{O}{\|}}{C}-OH \qquad (II)$$

c, d, and e, which may be identical or different, are each integers ranging from 0 to 20;
EO is an ethylene oxide group;
PO is a propylene oxide group; and
R" is chosen from optionally substituted divalent hydrocarbons and optionally substituted divalent aromatic groups;

with the proviso that at least one of the R groups is chosen from groups of formula (II) and with the proviso that when only one of the R groups is chosen from groups of formula (II), the other R groups are not all methyl groups; and (ii) silicone compounds of formula (V) and salts thereof:

$$H_3C-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_b-\left[O-\underset{\underset{\underset{\underset{O-(AO)_x-\overset{\overset{O}{\|}}{C}-R''-\overset{\overset{O}{\|}}{C}-OH}{|}}{(CH_2)_3}}{|}}{\overset{\overset{CH_3}{|}}{Si}}\right]_a-O-\underset{\underset{CH_3}{|}}{\overset{\overset{CH_3}{|}}{Si}}-CH_3 \qquad (V)$$

wherein:
a is an integer ranging from 1 to 100;
b is an integer ranging from 0 to 500;
AO is chosen from groups of formula (VI):

$$-(EO)_c-(PO)_d-(EO)_e- \qquad (VI)$$

c, d, and e, which may be identical or different, are each integers ranging from 0 to 20;
EO is an ethylene oxide group;
PO is a propylene oxide group; and
R" is chosen from optionally substituted divalent hydrocarbons and optionally substituted divalent aromatic groups; and (b) at least one amine compound comprising at least two amino groups, wherein said at least two amino groups are identical or different; and wherein said at least one silicone compound and said at least one amine compound are present in a combined amount effective to condition the at least one keratinous fiber, with the proviso that when said at least one silicone compound is chosen from silicone compounds of formula (V) and salts thereof then said at least one amine compound is not wheat protein or soy protein.

33. A method according to claim 32, further comprising wetting said at least one keratinous fiber with water prior to said application.

34. A method according to claim 32, further comprising rinsing said at least one keratinous fiber subsequent to said application.

35. A kit for caring for, treating, conditioning or durably conditioning at least one keratinous fiber comprising at least two compartments, wherein a first compartment comprises at least one compound comprising at least one silicone compound comprising at least one carboxylic acid group chosen from:

(i) silicone compounds of formula (I) and salts thereof:

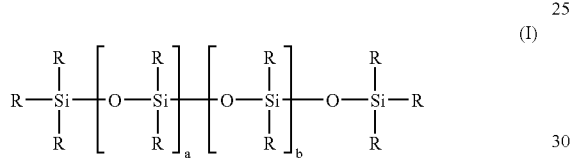

(I)

wherein:
a is an integer ranging from 1 to 100;
b is an integer ranging from 0 to 500;
R, which may be identical or different, are each chosen from optionally substituted hydrocarbon groups comprising from 1 to 9 carbon atoms, optionally substituted phenyl groups, and groups of formula (II):

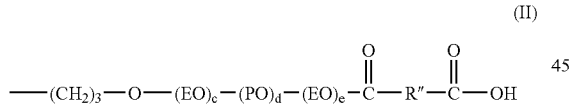

(II)

c, d, and e, which may be identical or different, are each integers ranging from 0 to 20;

EO is an ethylene oxide group;
PO is a propylene oxide group; and
R″ is chosen from optionally substituted divalent hydrocarbons and optionally substituted divalent aromatic groups;

with the proviso that at least one of the R groups is chosen from groups of formula (II) and with the proviso that when only one of the R groups is chosen from groups of formula (II), the other R groups are not all methyl groups; and (ii) silicone compounds of formula (V) and salts thereof:

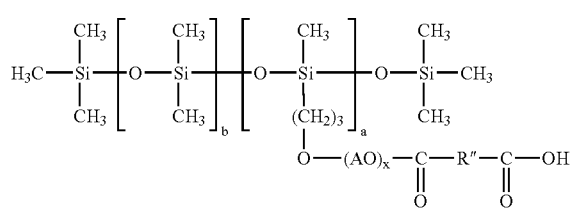

(V)

wherein:
a is an integer ranging from 1 to 100;
b is an integer ranging from 0 to 500;
AO is chosen from groups of formula (VI):

(VI)

c, d, and e, which may be identical or different, are each integers ranging from 0 to 20;
EO is an ethylene oxide group;
PO is a propylene oxide group; and
R″ is chosen from optionally substituted divalent hydrocarbons and optionally substituted divalent aromatic groups;

with the proviso that when said at least one silicone compound is chosen from silicone compounds of formula (V) and salts thereof then said at least one amine compound is not wheat protein or soy protein;

wherein a second compartment comprises at least one amine compound comprising at least two amino groups; and wherein the at least two amino groups are identical or different.

* * * * *

UNITED STATES PATENT AND TRADEMARK OFFICE
CERTIFICATE OF CORRECTION

PATENT NO. : 7,122,174 B2  Page 1 of 1
APPLICATION NO. : 10/259742
DATED : October 17, 2006
INVENTOR(S) : Nghi van Nguyen et al.

It is certified that error appears in the above-identified patent and that said Letters Patent is hereby corrected as shown below:

Claim 3, col. 18, line 20, "dumbly" should read --durably--.

Claim 5, col. 18, line 35, after ";" insert --and--.

Claim 29, col. 22, line 33, "comprising;" should read --comprising:--.

Signed and Sealed this

Sixth Day of February, 2007

JON W. DUDAS
*Director of the United States Patent and Trademark Office*